United States Patent
Kohlrausch et al.

(10) Patent No.: US 9,659,149 B2
(45) Date of Patent: May 23, 2017

(54) MEDICAL MONITORING SYSTEM BASED ON SOUND ANALYSIS IN A MEDICAL ENVIRONMENT

(71) Applicant: KONINKLIJKE PHILIPS N.V., Eindhoven (NL)

(72) Inventors: Armin Gerhard Kohlrausch, Eindhoven (NL); Thomas Falck, Eindhoven (NL); Albertus Cornelis Den Brinker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 367 days.

(21) Appl. No.: 14/351,603

(22) PCT Filed: Sep. 25, 2012

(86) PCT No.: PCT/IB2012/055090
§ 371 (c)(1),
(2) Date: Apr. 14, 2014

(87) PCT Pub. No.: WO2013/057608
PCT Pub. Date: Apr. 25, 2013

(65) Prior Publication Data
US 2014/0275856 A1    Sep. 18, 2014

Related U.S. Application Data

(60) Provisional application No. 61/547,914, filed on Oct. 17, 2011.

(51) Int. Cl.
G06N 5/02     (2006.01)
G06F 19/00    (2011.01)
(Continued)

(52) U.S. Cl.
CPC ............ G06F 19/34 (2013.01); A61B 5/0077 (2013.01); A61B 5/0205 (2013.01);
(Continued)

(58) Field of Classification Search
None
See application file for complete search history.

(56) References Cited

U.S. PATENT DOCUMENTS 6,790,183 B2 * 9/2004 Murphy ................. A61B 5/061
600/532
8,635,065 B2 * 1/2014 Goronzy-Thomae ... G10L 15/00
704/201

(Continued)

OTHER PUBLICATIONS

Kahn et al. "Identification and Modification of Environmental Noise in an ICU Setting", CHEST, 1998, pp. 535-540.*
(Continued)

*Primary Examiner* — Li-Wu Chang

(57) ABSTRACT

The invention relates to a medical monitoring system (100) based on sound analysis in a medical environment. A sound level analyzer (SLA, 10) is capable of providing an indicator for perceived levels of sound from a number of sound events, and a data storage modality (DSM, 20) is receiving and storing said indicator for perceived levels of sound and also corresponding information from an associated patient monitoring system (PMS, 60) handling information indicative of a physical and/or mental condition of a patient under influence by sound. A sound event analyzer (SEA, 30) is further being arranged for performing, within a defined time window, an overall sound analysis (ANA, 50) related to physical and/or mental condition of the patient that may be influenced by sound in order to assist or supervise medical personal with respect to the acoustic environment.

16 Claims, 3 Drawing Sheets

(51) Int. Cl.
*A61B 5/11* (2006.01)
*A61B 5/16* (2006.01)
*A61B 5/0205* (2006.01)
*A61B 5/0402* (2006.01)
*A61B 5/0476* (2006.01)
*A61B 5/0488* (2006.01)
*A61B 5/0496* (2006.01)
*A61B 5/00* (2006.01)
*A61B 5/0432* (2006.01)
*A61B 5/0484* (2006.01)

(52) U.S. Cl.
CPC .......... *A61B 5/0402* (2013.01); *A61B 5/0476* (2013.01); *A61B 5/0488* (2013.01); *A61B 5/0496* (2013.01); *A61B 5/1118* (2013.01); *A61B 5/165* (2013.01); *A61B 5/4815* (2013.01); *A61B 5/4884* (2013.01); *G06F 19/3406* (2013.01); *A61B 5/0006* (2013.01); *A61B 5/0432* (2013.01); *A61B 5/04845* (2013.01); *A61B 2505/03* (2013.01); *A61B 2560/0242* (2013.01)

(56) References Cited

U.S. PATENT DOCUMENTS

| | | | |
|---|---|---|---|
| 2002/0016568 A1* | 2/2002 | Lebel | A61M 5/172 604/131 |
| 2002/0171551 A1 | 11/2002 | Eshelman | |
| 2006/0012478 A1* | 1/2006 | Carmichel | G08B 3/10 340/552 |
| 2008/0146890 A1 | 6/2008 | LeBoeuf | |
| 2008/0157956 A1 | 7/2008 | Radivojevic | |
| 2009/0005657 A1 | 1/2009 | Bodlaender | |
| 2009/0228272 A1* | 9/2009 | Herbig | G10L 25/78 704/233 |
| 2011/0015495 A1 | 1/2011 | Dothie | |
| 2013/0310657 A1* | 11/2013 | Sullivan | A61B 5/6892 600/301 |

OTHER PUBLICATIONS

Ryherd et al., "Characterizing noise and perceived work environment in a neurological intensive care unit", J. Acoustic Soc. Am. 2008, pp. 747-756.*
MacKenzie, et al "Noise Levels and Noise Sources in Acute Care Hospital Wards", Building Serv. Eng. Res. Technology, vol. 28, No. 2, 2007, pp. 117-131.
Ryherd, E et al "Characterizing Noise and Perceived Work Environment in a Neurological Intensive Care Unit", Journal of Acoustical Society of America, vol. 123, No. 2, 2008, pp. 747-756.
Lawson, Nancy et al "Sound Intensity and Noise Evaluation in a Critical Care Unit", American Jounal of Critial Care, vol. 19, 2010, pp. 88-98.
Aitken, R.J. "Quantitative Noise Analysis in a Modern Hospital", Archives of Environmental Health, vol. 37, No. 6, 1982, pp. 361-364.
Elliott, Rosalind M. et al "A Pilot Study of Sound Levels in an Australian Adult General Intensive Care Unit" Noise & Health, vol. 12, No. 46, 2010, p. 26-36.
Christensen, Martin et al "Noise Levels in a General Surgical Ward: A Descriptive Study" Journal of Clinical Nursing, vol. 14, 2005, pp. 156-164.

* cited by examiner

Room #4                     8 hrs / 24 hrs / 3 days

1) Avg. noise level: High (60 dBA)

2) Avg. restorative period
   (Leq<50 dBA longer than 5 min)

20 min. (day) / 25 min (night)

3) Total restorative period (%)

15 % (day) / 35 % (night)

4) Noise sources affecting patient's sleep/rest quality
   - Speech (avoidable) : 35%      (avg. 65 dBA)
   - Alarm                  : 15%      (avg. 55 dBA)
   - Medical device         : 8%       (avg. 45 dBA)

5) Predicted sleep/rest quality: Poor

MEDICAL MONITORING SYSTEM BASED ON SOUND ANALYSIS IN A MEDICAL ENVIRONMENT

CROSS-REFERENCE TO PRIOR APPLICATIONS

This application is the U.S. National Phase application under 35 U.S.C. §371 of International Application No. PCT/IB2012/055090, filed on Sep. 25, 2012, which claims the benefit of U.S. Provisional Patent Application No. 61/547,914, filed on Oct. 17, 2011. These applications are hereby incorporated by reference herein.

FIELD OF THE INVENTION

The present invention relates to a medical monitoring system based on sound analysis in a medical environment. The present invention also relates to a corresponding method for providing monitoring based on sound analysis in a medical environment, and a corresponding computer program product for implementing the invention.

BACKGROUND OF THE INVENTION

Noise levels in hospital setting may be surprisingly high, especially in intensive care units (ICU). Recent research studies also indicate that patients are negatively impacted by the high noise levels. Major noise sources in ICU environments may be attributed to the behavior of staff, including speech and other activities.

MacKenzie et al. ("Noise levels and noise sources in acute care hospital wards," Building Serv. Eng. Res. Technol. 28, 2 (2007) pp. 117-131) have for example observed and classified noise sources in three 24-hour sessions in ICUs, and have identified a considerable number of avoidable, high-level noise events: rubbish bins, chair scraping, door closing/squeaking, cupboard door, and even opening of ring binders. A total of 30% of all noise events were characterized as totally avoidable, and a similar percentage as partially avoidable (like alarms; dropping objects; phone ringing).

There exist noise-level monitoring systems that measure the sound level in building spaces and provide real-time monitoring but these monitoring systems are typically not very specific about the source of the noise, rendering improvements and mitigation measures difficult to find.

However, the overall sound level is typically the only parameter on which such systems are designed to operate, and consequently the monitoring may often be too ambiguous, providing little information on what the actual noise sources are.

Additionally, the caretakers of patients, e.g. nurses, may not obtain valuable information about the sleep/rest quality of the patients that could be jeopardized by undesirable sounds i.e. noise.

The inventors of the present invention have appreciated that an improved medical monitoring system and method is of benefit, and has in consequence devised the present invention.

SUMMARY OF THE INVENTION

It would be advantageous to achieve an intelligent way of providing monitoring based on sound analysis in a medical environment. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

Thus, the above described object and several other objects are intended to be obtained in a first aspect of the invention by providing a medical monitoring system based on sound analysis in a medical environment, the system comprising:

a sound level analyzer (SLA), the sound-level analyzer being arranged for receiving an audio signal indicative of sound near a patient, the sound-level analyzer being capable of providing an indicator of perceived sound levels from a number of sound events, and a data storage modality (DSM), the data storage modality being arranged for receiving and storing said indicator for perceived levels of sound from the number of sound events from the sound level analyzer, and receiving and storing corresponding information from an associated patient monitoring system (PMS) handling information indicative of a physical and/or mental condition of a patient under influence by sound, and a sound event analyzer (SEA), the sound event analyzer receiving from the data storage modality said indicator for perceived levels of sound from the number of sound events, and corresponding information from the associated patient monitoring system (PMS), the sound event analyzer further being arranged for performing, within a defined time window, an overall sound analysis related to physical and/or mental condition of the patient that may be influenced by sound.

The invention is particularly, but not exclusively, advantageous for obtaining a monitoring system in a medical context, where both information indicative of physical and/or mental condition of a patient under influence by sound, and information related to the perceived level of sound from a number of sound events can be combined into a more advanced assessment of the patient's overall condition than hitherto possible.

For example, a simple average of noise level would not be so informative, as the patient's sleep/rest condition may not be so relevant to the average noise level but more to the continuous time duration available during which the noise level is below a certain threshold value and how fragmented such durations are. When it comes to the patient sleep quality, for example, this so-called restorative period needs to be related also to the patient sleep cycle, to accurately predict the actual effect of noise on sleep, cf. Ryherd, E.; Waye, K. P.; Ljungkvist, L. "Characterizing noise and perceived work environment in a neurological intensive care unit," Journal of Acoustical Society of America, 123(2), 747-756, 2008. This is facilitated and made possible using the advantageous teaching of the present invention.

Thus, the present invention may provide a long-term overview of acoustic environment in patient rooms. This monitoring system may be seen as an "environmental dosimeter" for patients aimed to inform the medical staff of the predicted sleep/rest quality that is directly affected by undesirable sound e.g. noisy events, and this information can be used to adjust their patient-care-treatment routines, e.g. delaying washing the patient to compensate for a bad night and so forth.

The patient monitoring system is, per se, another entity but could also be an integral part of the monitoring system, or verse visa. The patient monitoring system may comprise, or be communicatively arranged with, various sensors for obtaining relevant patient data, e.g. electrical sensors, mechanical sensors, biochemical sensors. In a particular embodiment, the patient monitoring system may receive input based on manual observations, e.g. from a nurse.

The present invention may be applied on a single patient, or on a group of patients depending on the circumstances. For example, a group of patients sharing a room, or having neighboring rooms, may have similar acoustical environment.

Typically, the sound-level analyzer may comprise a psychoacoustic model for providing an indicator for perceived loudness, e.g. conventionally A or B weighting, or alternatively Zwicker loudness, or other hearing models readily available to the skilled person in acoustics. Possibly, more advanced models based on noisiness, sharpness, roughness, etc. may be applied within the teaching of the present invention. More alternative, a measure of the accumulated acoustic dose may be implemented in the psychoacoustics model.

Beneficially, the associated patient monitoring system (PMS) may comprise information related to the physical activity level of the patient, such as information indicative of sleep and/or rest. It may be particularly mentioned that information relevant for the mental/physical condition of a sedated patient may also be obtained, stored in the patient monitoring system. Particularly, the associated patient monitoring system (PMS) may comprise information obtainable from the list comprising: electrodiagnosis, such as EEG, ECG, EOG, EMG, actigraphy, movement detection, video-based monitoring and/or sound-based monitoring. It may be mentioned that video-monitoring may include infrared (IR) monitoring. Likewise, sound monitoring may include ultrasound monitoring.

In a particular advantageous embodiment, the sound level analyzer may be cooperating with a sound scene analyzer (SSA), the sound scene analyzer also being arranged for receiving said audio signal indicative of sound near a patient in the medical environment and being capable of analyzing and classifying the audio signal so as to obtain a list of one, or more, sound sources in the medical environment surrounding the patient. The sound scene analyzer may be part of an alternative feedback system for providing immediate feedback in response to undesirable sounds i.e. noise. Notice that the sound scene analyzer may also be located outside the monitoring system of the present invention.

Beneficially, the classifying of said one, or more, sound sources may be applied in the overall sound analysis to identify possible sources of negative influence on the rest and/or sleep of said patient to improve overall health and recovery.

Particularly, the overall sound analysis may comprise information related to the quality and/or quantity of the rest and/or sleep of the patient. More advantageously, the overall sound analysis may comprise a measure of one or more of the following non-limiting indicators;
  average sound level
  sound impact based on said perceptual model
  estimate of restorative period(s)
  estimated annoyance, and/or
  an overall sleep/rest indicator, possibly a qualitative indicator.

The medical monitoring system (100) according to claim 1, wherein the monitoring system is arranged for monitoring a first plurality of patients with a second plurality of microphones, the microphones being arranged for communication with the monitoring system.

Preferably, the monitoring system may be arranged for monitoring a first plurality of patients with a second plurality of microphones, i.e. the number of microphones need not be equal to the number of patient. The microphones are arranged for communication with the monitoring system, either by wire or wirelessly as will be readily appreciated by the skilled person. In one embodiment, there may also be just one patient and one microphone, e.g. a single patient approach for bed side application, for example in a private home.

Preferably, the monitoring system may be arranged for communication with one or more communication devices, the communication devices being utilizable by medical personal, visitors, and/or patients. The communication devices are arranged for communication with the monitoring system, either by wire or wirelessly as will be readily appreciated by the skilled person. For example as mobile phones, monitors etc.

In a second aspect, the present invention relates to a method for operating a medical monitoring system based on sound analysis in a medical environment, the method comprising:
  providing a sound level analyzer (SLA), the sound-level analyzer being arranged for receiving an audio signal indicative of sound near a patient, the sound-level analyzer being capable of providing an indicator for perceived levels of sound from a number of sound events, and
  providing a data storage modality (DSM), the data storage modality being arranged for receiving and storing said indicator for perceived levels of sound from the number of sound events from the sound level analyzer, and receiving and storing corresponding information from an associated patient monitoring system (PMS) handling information indicative of physical and/or mental condition of a patient under influence by sound, and
  providing a sound event analyzer (SEA), the sound event analyzer receiving from the data storage modality said indicator for perceived levels of sound from the number of sound events, and corresponding information from the associated patient monitoring system (PMS), the sound event analyzer further being arranged for performing, within a defined time window, an overall sound analysis (ANA) related to physical and/or mental condition of the patient that may be influenced by sound.

In a third aspect, the invention relates to a computer program product being adapted to enable a computer system comprising at least one computer having data storage means in connection therewith to control a medical monitoring system based on sound analysis in a medical environment according to the second aspect. This aspect of the invention is particularly, but not exclusively, advantageous in that the present invention may be accomplished by a computer program product enabling a computer system to carry out the operations of the system of the first aspect of the invention when down- or uploaded into the computer system. Such a computer program product may be provided on any kind of computer readable medium, or through a network.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
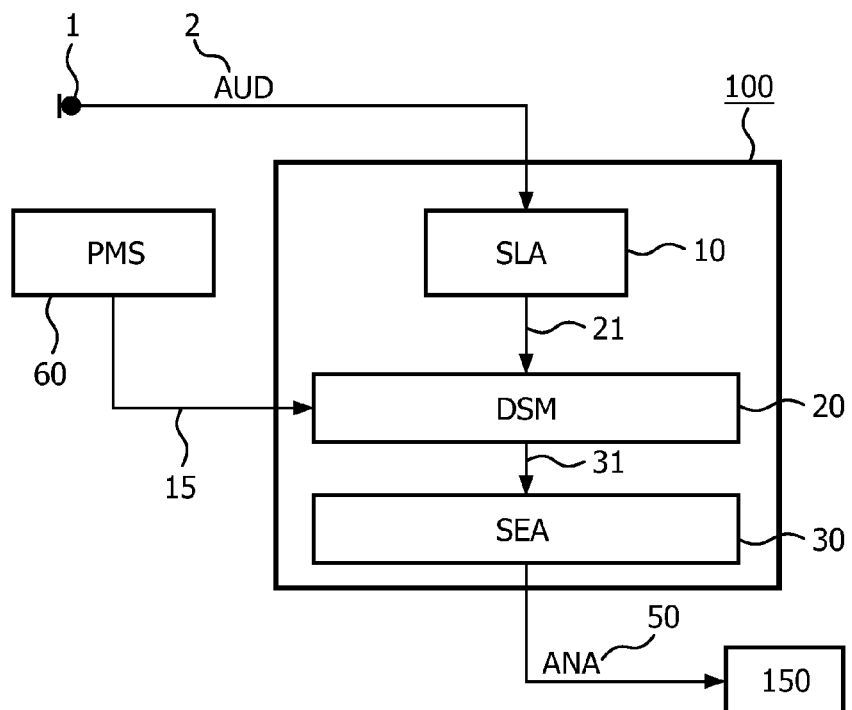
FIG. 1 shows a schematic drawing of a monitoring system 100 according to the present invention.

FIG. 1 shows a schematic drawing of a monitoring system 100 according to the present invention.

The system comprises a sound level analyzer SLA 10, the sound-level analyzer being arranged for receiving an audio signal AUD 2 indicative of sound near a patient (not shown), the sound-level analyzer being capable of providing an indicator for perceived levels of sound from a number of sound events, e.g. wherein the sound level analyzer have an appropriate perceptual model for providing perceived loudness. It should be noted that the SLA may provide a plurality of indicators for perceived loudness, e.g. for various time windows, and/or different frequency bands. Notice that the SLA does typically not know beforehand what the actual number of sound events is.

Additionally, the system 100 has a data storage modality DSM 20, the data storage modality being arranged for receiving and storing said indicator for perceived levels of sound from the number of sound events from the sound level analyzer SLA, as indicated by arrow 21. Moreover, the DMS is receiving and storing corresponding information from an associated patient monitoring system PMS 60 handling information indicative of physical and/or mental condition of a patient under influence by sound, as schematically indicated by arrow 15. Notice that the PMS is not part of the monitoring system as such, rather the PMS is associated with the monitoring system in the sense that the monitoring system and the PMS are mutually arranged for communication but they are typically separate entities.

Furthermore, a sound event analyzer SEA 30 is provided, the sound event analyzer receiving from the data storage modality DSM 10 said indicators for perceived levels of sound from the number of sound events, and corresponding information from the associated patient monitoring system PMS 60, the sound event analyzer SEA 30 further being arranged for performing, within a defined time window, e.g. some hours, or a few day, an overall sound analysis ANA 50 related to physical and/or mental condition of the patient that may be influenced by sound. The analysis is typically forwarded for display and further medical assessment in communication devices 150.

Figure 2:
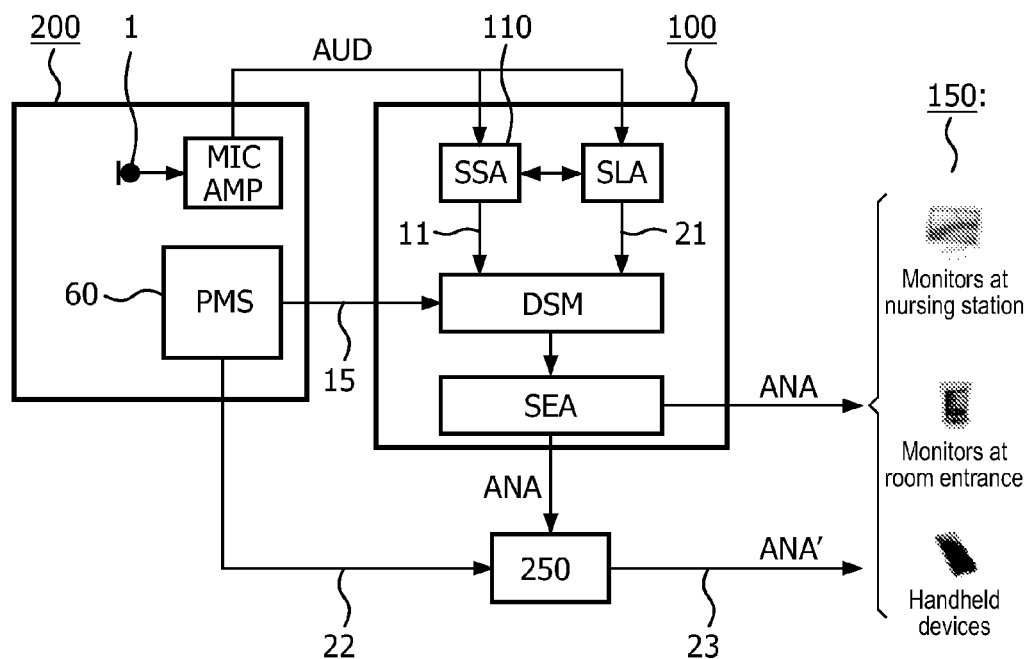
FIG. 2 shows a more detailed embodiment of the monitoring system 100 according to the present invention.

FIG. 2 shows a more detailed embodiment of the monitoring system 100 according to the present invention. In addition to the elements shown in FIG. 1, FIG. 2 also shows a patient room 200 where a microphone 1 with microphone amplifier MIC AMP is positioned. Furthermore, the sound level analyzer SLA 10 is advantageously cooperating with a sound scene analyzer SSA 110, the sound scene analyzer also being arranged for receiving said audio signal AUD indicative of sound near a patient in the medical environment and being capable of analyzing and classifying the audio signal so as to obtain a list of one, or more, sound sources in the medical environment surrounding the patient (not shown). Furthermore, the medical monitoring system 100 will therefore be able to assist and/or perform the classifying of said one, or more, sound sources that can be applied in the overall sound analysis ANA to identify possible sources of negative influence on the rest and/or sleep of said patient.

The inventors have appreciated that the objective of improving the hospital environment by sound analysis in a monitoring system 100 requires a targeted approach. To start with, the indicators to the staff have to be meaningful (interpretable by these people) and also they may be related to sound events which are within their span of control. Furthermore, the indicators should adequately capture the negative impact of the sound on the patient (meaningful).

These considerations already indicate that mere sound level monitoring is not sufficient. It also leads to a classification scheme which differs fundamentally from those found elsewhere, e.g. music analysis. Also, the span-of-control issue led to the division of distributing sound into avoidable and unavoidable classifications with the combined operation of the SSA and the SLA. These considerations together with a screening of sound recordings made in the hospital led the present inventors to define a number of hospital specific classes and means or combination of means for identifying these avoidable and unavoidable classifications.

There are classes of sound events that frequently happen in hospital environments, some of which, the inventors have found, may have significant impact on patient well-being not only due to their contribution to the overall noise level, but also due to their particular temporal and spectral characteristics (e.g. impulsiveness, etc.). By automatically identifying such classes of noise sources and notifying medical staff of their potential impact, therefore, subjective noise annoyance level can effectively be reduced, thus improving patients' sleep/rest quality, which may also positively influence on their recovery speed. In particular, the inventors have identified the following, non-exhaustive list of classes, which the monitoring system will be trained to identify:

Speech (Patient-Involved and Others)

From their own recordings and analysis of hospital noise, the inventors have identified that speech activities are the most dominant noise sources in terms of the average noise level. Therefore, it is important to discriminate speech from non-speech sounds. To detect the speech within the input signal, one may use several features including pitch range, mel-frequency cepstral coefficients (MFCC) and envelope variation. It is difficult to distinguish avoidable/non-avoidable speech since the context of the conversation should also be taken into account. Accordingly, the inventors' approach, instead, is to identify patient-involved speech activities that are obviously unavoidable (from the patient's point of view), where other speech activities (e.g. between hospital staff) can be considered to be at least partly avoidable. In order to distinguish patient-involved conversation, various ways may be used, one of which can be a dedicated beam-forming technique using a multiple microphones, capturing audio signals only from a very limited area (the head of the patient bed). One of other examples can be the use of speaker identification technique. If the audio input is classified as speech, and if the input from the beam-former (or speaker identifier) indicates that it comes from the patient, then the system assumes that patient himself/herself is speaking. Once patient speech is detected, all speech activities around the detected time (e.g. 5-10 minutes) will be considered to be patient-involved speech. Therefore, at the end of this process, speech will be further classified as patient-involved speech and other speech activities.

Alarms

Alarm is also one of the dominant noise sources in hospital. By producing alarm sounds, monitoring devices deliver warnings to medical staff. However, not all of the alarm sounds are unavoidable, since it was learned from field studies (and also from literature) that some less-urgent alarms (e.g. signaling the end of injection, etc.) are simply ignored without immediate actions taken by nursing staff. First, the classifier will identify all alarm sounds especially analyzing the tonality, harmonic structure and repetitiveness of input signal. Then, the system will observe how long the alarm sound continues without staff intervention. If the alarm lasts longer than a pre-determined threshold, then it will be detected and registered as an avoidable event. Also, the system can get the history of alarm sounds from patient monitoring systems, and learn how urgently (in medical sense) they have been reacted upon, based on which the threshold time for each type of alarm sound can be adjusted. It should however be very clear that the monitoring system will only register the annoyance level of alarm sounds without any indication of the severity of medical situation (for example, the monitoring system will never operate to force medical staff to mute essential alarms).

Medical Equipment Noise (e.g. Mechanical Ventilator)

For the patients in acute phases, e.g. those in intensive care unit, various medical devices are used to support their lives. However, these devices may constantly generate noise in the vicinity of patients' ears due to their positions in the room, which will negatively impact on their sleep/rest quality. Since the noise from such devices is continuous and repetitive, the monitoring system will classify this class of noise based on rhythmicity and predictability.

Footsteps

For easy maintenance of hygiene, vinyl floor is common in hospital, which creates very distinctive footstep noises, which, it was observed, significantly contributes to the overall noise annoyance, although the average noise level is not so high. The monitoring system will use the rhythmicity and spectral contents (e.g. MFCC), in order to learn and identify footsteps in a particular hospital environment.

Building Parts e.g. Door/Drawer/Cupboard Opening and Closing; Object Dropping; Thumps Similar to footsteps, this class of sound events does not contribute much to the average noise level, but have significant impact on patient sleep/rest quality due to the impulsiveness causing high instantaneous peak noise level. The monitoring system will classify these events based on the measures of onset steepness and percussiveness.

Noise from Metallic Objects (e.g. Trolley, Bed Frame, etc.)

Similar to the two above classes, the physical level of metallic object noise may not be so high, but due to its unique timbre, the resultant annoyance may be significant. In order to identify this class of sound events, the monitoring system will detect sharp spectral peaks that are not harmonics of each other.

Computer Related Events, e.g. Mouse Clicking

From the inventors' own sound recordings, mouse clicking (dragging) noise was identified to be very disturbing (due to the proximity to patients' ears, as LCD monitor with mouse is commonly positioned to the bedside for nursing staff to access patient data), but hardly recognized as a potentially severe noise source. Very unique temporal spectral characteristics of mouse clicking noise will be used for the classification, which also partly adopts techniques developed to identify keyboard strike noise.

Music from TV/Radio

Sounds from TV or radio, when unwanted (e.g. coming from neighboring room) can be very disturbing. As speech in TV/radio contents may already be classified as 'Other speech activities', the monitoring system will, instead, attempt to distinguish music from non-music contents, based on similar features that are used for the detection of speech (e.g. envelope variation of music is less than that of speech).

Most of the features described for the above classes are commonly used, for example, in speech analysis, music information retrieval, music recommendation system and other research areas (keyboard stroke). Their combination however, and adaptation and optimization of the combination particularly for tailored classes (based on the meaningful impact, staff-interpretable, span-of control) for the hospital environments is an inventive step.

The following table summarizes the classes of sound events that may be used by the monitoring system 100 and associated dominant class features:

| No. | Class of sound events | Features relevant for the classification | Remarks |
| --- | --- | --- | --- |
| 1 | Speech | Pitch range, mel-frequency cepstral coefficients (MFCC) and envelope variation | Patient-involved speech will be identified by, e.g., beam-forming techniques or speaker identification. |
| 2 | Alarm | Tonality, harmonic structure and repetitiveness | The system will learn potentially avoidable alarms based on the information from patient monitoring systems. |
| 3 | Medical equipment noise | Rhythmicity and predictability | |
| 4 | Footsteps | Rhythmicity and spectral contents (e.g. MFCC) | |
| 5 | Building parts opening and closing; object dropping; thumps | Onset steepness and percussiveness | |
| 6 | Noise from metallic objects | Non-harmonic sharp spectral peaks | |
| 7 | Computer relevant events | Temporal spectral characteristics | |
| 8 | Music from TV/Radio | Features used for speech detection (e.g. envelope variation) | |

It should be noted that identified sound events from the list of sound sources are further classified into avoidable unavoidable sound sources, possibly noise. If the classification by the sound scene analyzer SSA is sufficiently accurate, some sound events may be easy to classify at this stage as avoidable or unavoidable. For example, object-dropping sound can be identified by the analyzer, and can directly be classified as avoidable. On the other hand, additional information may be required for this intelligent classification. To distinguish essential alarm sounds from unnecessary ones, for example, the sound event analyzer SEA may have to be trained based on the information from a patient monitoring systems PMS and/or a hospital central monitoring database 250 (cf. FIG. 2): which alarm sounds the hospital staff had quickly responded to, given the condition of patient. A speaker identification system may also be employed to differentiate avoidable speech activities from the unavoidable (for example, a conversation in which the patient is involved is unavoidable). In addition, data from sleep/rest monitoring devices (e.g. based on actigraphy, electrodiagnosis (incl. EEG, ECG, EOG, EMG, etc.), camera-based movement detection, etc.) can be used to more accurately evaluate the influence of noise, which depends on the patient's state.

Though the monitoring system 100 is shown as a separate entity, it is contemplated that the present invention may readily be integrated together with, or as a part of, the central monitoring and surveillance unit 250 of the hospital or medical environment being monitored. Alternatively, the present invention may readily be integrated with, or as a part of, the patient monitoring system PMS 60. Alternatively, it is contemplated that the present invention may readily be integrated together with, or as a part of, a communication device 150, e.g. as a part of a mobile device/phone, having sufficient computational resources and communicative abilities for implementing the teaching of the present invention.

The central monitoring and surveillance unit 250 of the hospital or medical environment being monitored will typically receive information from the patient monitoring system PMS as indicated by arrow 22. Optionally, it is contemplated that the central monitoring and surveillance unit 250 may receive analysis result ANA and further generate supplementary analysis ANA' that may be transmitted to the communication devices 150 as indicated by arrow 23.

Figure 3:
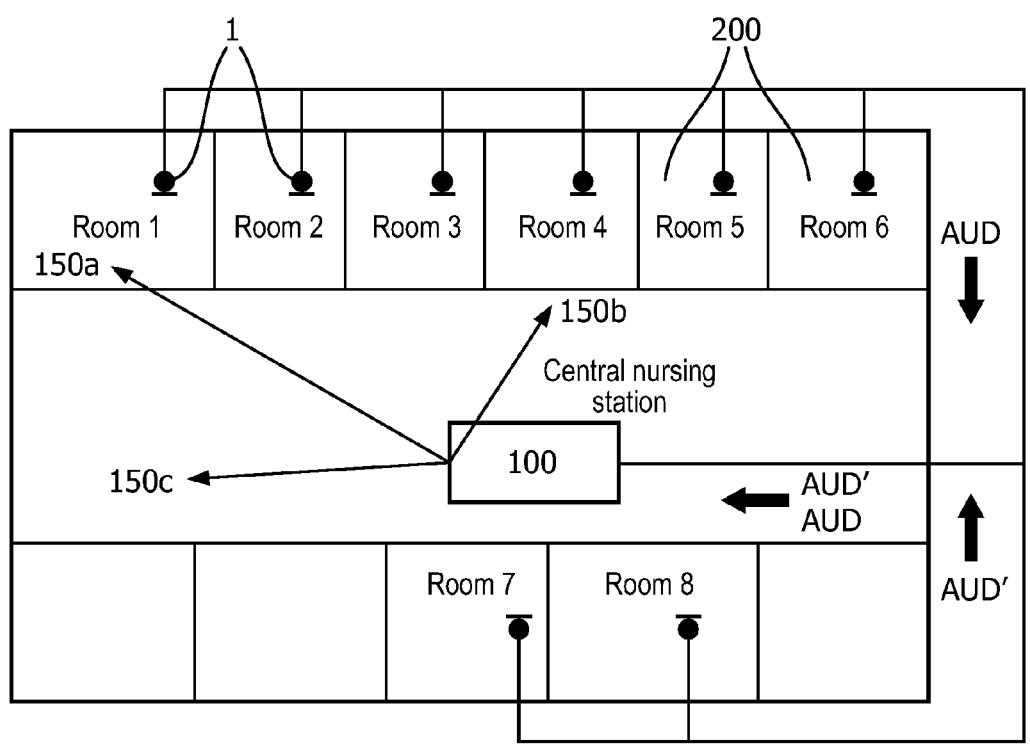
FIG. 3 shows an embodiment of the monitoring system 100 according to the present invention implemented in a hospital environment with different patient rooms 200.

FIG. 3 shows an embodiment of the monitoring system 100 according to the present invention implemented in a hospital environment with different patient rooms 200 (numbered Room 1 to Room 8) shown in the layout of a medical department, each room 200 having a microphone 1 as shown. Also three different monitoring devices 150 are shown receiving monitoring signal from the system 100 as indicated by the shown arrows, e.g. communication device 150a could be display device in Room 1, communication device 150b could be a central display device for the medical department, and communication device 150c could be handheld device carried by a medical staff member (not shown).

Figures 4, 5:
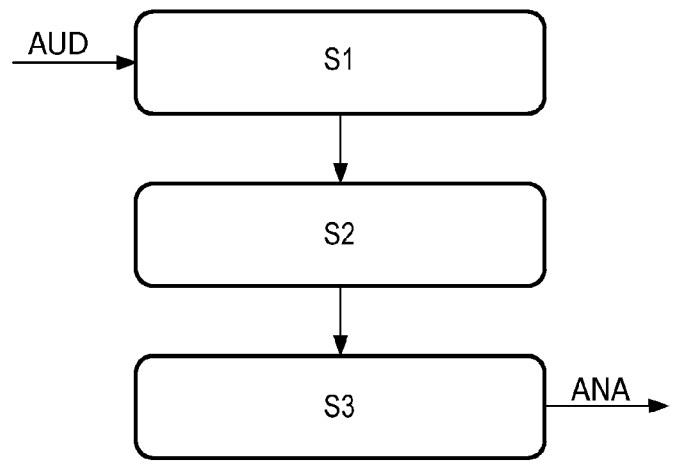
FIG. 4 shows a monitoring example from the monitoring system 100 provided an overview of noise levels and noise sources.
FIG. 5 is a schematic system-chart representing an outline of the operations of a method or a computer program product according to the present invention.

FIG. 4 shows a monitoring example from the monitoring system 100 provided an overview of noise levels and noise sources. As shown in FIG. 4, there may be listed in a purely illustrative manner: 1) average noise level, 2) average restorative periods (day/night intervals), 3) total restorative period (day/night intervals), 4) noise sources affecting patient sleep/rest quality, and 5) an overall sleep/rest indicator. In short, a restorative period can be defined as a continuous time duration during which the noise level is below a certain threshold. When requested, the stored information is retrieved and analyzed for a user-selected duration (e.g. 8 hours/24 hours/3 days).

FIG. 5 is a schematic system-chart representing an outline of the operations of a method, or a computer program product according to the present invention, the method comprising:

S1 providing a sound level analyzer SLA 10, the sound-level analyzer being arranged for receiving an audio signal indicative of sound near a patient, the sound-level analyzer being capable of providing an indicator for perceived levels of sound from a number of sound events, and S2 providing a data storage modality DSM 20, the data storage modality being arranged for receiving and storing said indicator for perceived levels of sound from the number of sound events from the sound level analyzer, and receiving and storing corresponding information from an associated patient monitoring system PMS 60 handling information indicative of a physical and/or mental condition of a patient under influence by sound, and S3 providing a sound event analyzer SEA 30, the sound event analyzer receiving from the data storage modality said indicator for perceived levels of sound from the number of sound events, and corresponding information from the associated patient monitoring system PMS, the sound event analyzer further being arranged for performing, within a defined time window, an overall sound analysis ANA 50 related to physical and/or mental condition of the patient that may be influenced by sound.

In short, the invention relates to a medical monitoring system 100 based on sound analysis in a medical environment. A sound level analyzer SLA 10 is capable of providing an indicator for perceived levels of sound from a number of sound events, and a data storage modality DSM 20 is receiving and storing said indicator for perceived levels of sound and also corresponding information from an associated patient monitoring system PMS 60 handling information indicative of a physical and/or mental condition of a patient under influence by sound. A sound event analyzer SEA 30 is further being arranged for performing, within a defined time window, an overall sound analysis ANA 50 related to physical and/or mental condition of the patient that may be influenced by sound in order to assist or supervise medical personal with respect to the acoustic environment.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

The invention claimed is:

1. A medical monitoring system comprising a digital data processor configured to implement:

a sound level analyzer configured to receive an audio signal from a medical environment surrounding a patient and provide an indicator for perceived levels of sound generated by sound events occurring in the medical environment;

a data storage modality configured to receive and store the indicator for the perceived levels of sound and corresponding information, obtained from an associated patient monitoring system, and indicative of at least one of physical or mental condition of the patient;

a sound event analyzer configured to perform an overall sound analysis related to the at least one of the physical or mental condition of the patient based on the indicator and the corresponding information stored in the data storage; and a sound scene analyzer configured to analyze and classify the audio signal, create a list of one or more sound sources that generate the sound events occurring in the medical environment surrounding the patient, and differentiate avoidable sources of negative influence on rest or sleep of the patient from unavoidable sources of negative influence, wherein the sound scene analyzer is configured to distinguish unavoidable and essential alarm sounds from avoidable and non-essential alarm sounds based on training information from at least one of a patient monitoring system or a hospital central monitoring database, and wherein the sound event analyzer is configured to identify the sound events occurring in the medical environment based on analyzing tonality, harmonic structure, rhythmicity, predictability, spectral content, measures of onset steepness, percussiveness, and repetitiveness of the audio signal.

2. The medical monitoring system of claim 1 wherein the sound level analyzer comprises a perceptual model for providing perceived loudness.

3. The medical monitoring system of claim 1 wherein the sound level analyzer is further configured to provide a measure of an accumulated acoustic dose.

4. The medical monitoring system of claim 1 wherein the associated patient monitoring system comprises information related to a physical activity level of the patient.

5. The medical monitoring system of claim 1 wherein the associated patient monitoring system comprises information comprising at least one of: sleep or rest monitoring devices, electrodiagnosis, including EEG, ECG, EOG, EMG, actigraphy, movement detection, video-based monitoring, or sound-based monitoring.

6. The medical monitoring system of claim 1 wherein the overall sound analysis comprises information related to at least one of quality or quantity of the rest or sleep of the patient.

7. The medical monitoring system of claim 6 wherein the overall sound analysis comprises a measure of one or more of:
average sound level;
sound impact based on perceptual model estimate of one or more restorative period;
estimated annoyance; or
an overall sleep or rest indicator, possibly a qualitative indicator.

8. The medical monitoring system of claim 1 further including one or more microphones, the one or more microphones being in communication with the monitoring system and configured to receive audio signals from the patient in the medical environment.

9. The medical monitoring system of claim 1 wherein the monitoring system is configured to communicate with one or more communication devices, the communication devices being accessible by at least one of medical personnel, visitors or patients.

10. A method for monitoring sound in a medical environment, the method comprising using a computer processor for:

receiving an audio signal from a medical environment surrounding a patient, and providing an indicator for perceived levels of sound generated by sound events occurring in the medical environment;

receiving and storing, in a data storage modality, the indicator for the perceived levels of sound and corresponding information, obtained from an associated patient monitoring system, and indicative of at least one of physical or mental condition of the patient;

performing an overall sound analysis related to the at least one of the physical and/or mental condition of the patient based on the indicator and the corresponding information stored in the data storage;

analyzing and classifying the audio signal;

creating a list of one or more sound sources that generate the sound events occurring in the medical environment surrounding the patient; and differentiating avoidable sources of negative influence on rest or sleep of the patient from unavoidable sources of negative influence;

wherein the analyzing and classifying step includes identifying alarm sounds generated in the medical environment based on at least one of the tonality, harmonic structure, and repetitiveness of the audio signal, and in an event an alarm sound is identified, distinguishing, in the differentiating step, avoidable alarm sounds from unavoidable alarm sounds by observing the duration of the identified alarm sound and determining whether the observed duration exceeds a predetermined duration, and wherein the predetermined duration is determined based on at least one of a history of alarm sounds previously generated in the medical environment or urgency of response previously given to a specific alarm sound.

11. A computer program product, tangibly embodied in a non-transitory computer readable storage medium, comprising instructions being operable to cause a data processing system to monitor sound in a medical environment according to claim 10.

12. The medical monitoring system of claim 1 wherein the sound scene analyzer is configured to differentiate avoidable sources of negative influence from unavoidable sources based on known temporal and spectral characteristics of the sound events, the temporal and spectral characteristics including at least one of pitch range of speech, mel-frequency cepstral coefficients of speech, and envelope variation of speech.

13. The medical monitoring system of claim 1 wherein the sound scene analyzer is configured to differentiate avoidable speech from unavoidable speech involving the patient.

14. The medical monitoring system of claim 13 wherein the sound scene analyzer is configured to differentiate avoidable speech from unavoidable speech involving the patient based on a dedicated beamforming technique using one or more microphones that capture audio signals produced in close vicinity of the patient.

15. The medical monitoring system of claim 1 wherein the sound event analyzer is configured to identify alarm sounds generated in the medical environment based on at least one of the tonality, harmonic structure, and repetitiveness of the audio signal, and in an event an alarm sound is identified, the sound scene analyzer is configured to distinguish avoidable alarm sounds from unavoidable alarm sounds by observing the duration of the identified alarm sound and determining whether the observed duration exceeds a predetermined duration.

16. The medical monitoring system of claim 15 wherein the sound event analyzer is configured to determine the predetermined duration based on at least one of a history of alarm sounds previously generated in the medical environment or urgency of response previously given to a specific alarm sound.

* * * * *